US010542900B2

(12) United States Patent
Sattler et al.

(10) Patent No.: US 10,542,900 B2
(45) Date of Patent: Jan. 28, 2020

(54) DEVICE AND METHOD FOR DETECTING ELECTRIC POTENTIALS

(71) Applicant: Drägerwerk AG & Co. KGaA, Lübeck (DE)

(72) Inventors: Frank Sattler, Lübeck (DE); Marcus Eger, Lübeck (DE)

(73) Assignee: DRÄGERWERK AG & CO. KGAA, Lübeck (DE)

(*) Notice: Subject to any disclaimer, the term of this patent is extended or adjusted under 35 U.S.C. 154(b) by 505 days.

(21) Appl. No.: 15/324,448

(22) PCT Filed: Jul. 2, 2015

(86) PCT No.: PCT/EP2015/001340
§ 371 (c)(1),
(2) Date: Jan. 6, 2017

(87) PCT Pub. No.: WO2016/005036
PCT Pub. Date: Jan. 14, 2016

(65) Prior Publication Data
US 2017/0156624 A1 Jun. 8, 2017

(30) Foreign Application Priority Data
Jul. 7, 2014 (DE) .................. 10 2014 009 955

(51) Int. Cl.
*A61B 5/0428* (2006.01)
*A61B 5/04* (2006.01)
(Continued)

(52) U.S. Cl.
CPC ...... *A61B 5/04282* (2013.01); *A61B 5/04004* (2013.01); *A61B 5/04017* (2013.01);
(Continued)

(58) Field of Classification Search
CPC ............ A61B 5/04017; A61B 5/04085; A61B 5/7203; A61B 2562/04; H03F 3/45; H03F 3/45973; H03F 2203/45138
See application file for complete search history.

(56) References Cited

U.S. PATENT DOCUMENTS 4,448,202 A * 5/1984 Wajszczuk ......... A61B 5/04011
600/522
6,487,449 B1 * 11/2002 Kaiser .................. A61B 5/0424
600/547
(Continued)

FOREIGN PATENT DOCUMENTS

CN 101951832 A 1/2011
CN 201965171 U 9/2011
(Continued)

OTHER PUBLICATIONS

Jorgovanovic Nikola et al., A novel AC-amplifier for Electrophysiology: Active DC Suppression with Differential to Differential Amplifier in the Feedback-loop, 2001 Proceedings of the 23rd Annual EMBS International Conference, vol. 3, pp. 3328-3331.
(Continued)

*Primary Examiner* — Sean P Dougherty
(74) *Attorney, Agent, or Firm* — McGlew and Tuttle, P.C.

(57) ABSTRACT

A device for detecting electric potentials of the body of a patient has measuring electrode inputs ($Y_1$, . . . , $Y_n$) connected with and a plurality of outputs ($A_1$, . . . , $A_n$) via amplifiers ($Op_1$, . . . , $Op_n$). A summing unit (13) is connected with the outputs and outputs a mean value of the signals ($E_1$, . . . , $E_n$) output by the amplifiers. Common mode signals are removed from the signals ($E_1$, . . . , $E_n$) by a subtracting unit (19) which subtracts the output of the summing unit, amplified by an amplification factor ($1/\beta$), from at least a portion of the output of the subtracting unit. The output of the subtracting unit is connected with the
(Continued)

inputs of the amplifiers. The subtracting unit amplification factor (1/β) and an amplification (β') of the amplifiers for the output of the subtracting unit are adapted, such that the reciprocal value of the amplification factor (1/β) corresponds to the amplifiers amplification (β').

18 Claims, 4 Drawing Sheets

(51) Int. Cl.
  *A61B 5/00* (2006.01)
  *H03F 3/45* (2006.01)
  *A61B 5/0408* (2006.01)
  *A61B 5/0492* (2006.01)
  *H02M 1/12* (2006.01)

(52) U.S. Cl.
  CPC ........ *A61B 5/04085* (2013.01); *A61B 5/0492* (2013.01); *A61B 5/7203* (2013.01); *H03F 3/45* (2013.01); *H03F 3/45475* (2013.01); *H03F 3/45973* (2013.01); *A61B 2562/0209* (2013.01); *A61B 2562/04* (2013.01); *H02M 2001/123* (2013.01); *H03F 2200/261* (2013.01); *H03F 2203/45138* (2013.01); *H03F 2203/45521* (2013.01)

(56) References Cited

U.S. PATENT DOCUMENTS

| | | | | |
|---|---|---|---|---|
| 2009/0008654 | A1* | 1/2009 | Nagai | H01L 25/0753 257/88 |
| 2011/0288605 | A1* | 11/2011 | Kaib | A61B 5/0006 607/5 |
| 2012/0095361 | A1 | 4/2012 | Xu et al. | |
| 2014/0247058 | A1* | 9/2014 | Mortara | A61B 5/0424 324/601 |
| 2016/0113532 | A1* | 4/2016 | Sattler | A61B 5/04004 600/372 |
| 2016/0113547 | A1* | 4/2016 | Eger | A61B 5/0531 600/547 |

FOREIGN PATENT DOCUMENTS

| | | |
|---|---|---|
| CN | 202837375 U | 3/2013 |
| DE | 29 26 165 A1 | 1/1980 |
| EP | 2 442 443 A1 | 4/2012 |
| WO | 97/06728 A1 | 2/1997 |
| WO | 2009/000030 A1 | 12/2008 |
| WO | 2009/040697 A2 | 4/2009 |
| WO | 2013/133697 A1 | 9/2013 |

OTHER PUBLICATIONS

Nikola J et al: "A novel ac-amplifier for electrophysiology: active dc suppression with differential to differential amplifier in the feedback-loop", 2001 Conference Proceedings of the 23rd Annual International Conference of the IEEE Engineering in Medicine and Biology Society (Cat. No.01CH37272) vol. 3 ; [Annual International Conference of the IEEE Engineering in Medicine and Biology Society. EMBS], vol. 4, Oct. 25, 2001 (Oct. 25, 2001), pp. 3328-3331.

In-Duk Hwang et al: "Direct Interference Canceling for Two-Electrode Biopotential Amplifier", IEEE Transactions on Biomedical Engineering, IEEE Service Center, Piscataway, NJ, USA, va1. 55, No. 11, Nov. 1, 2008 (Nov. 1, 2008), pp. 2620-2627.

* cited by examiner

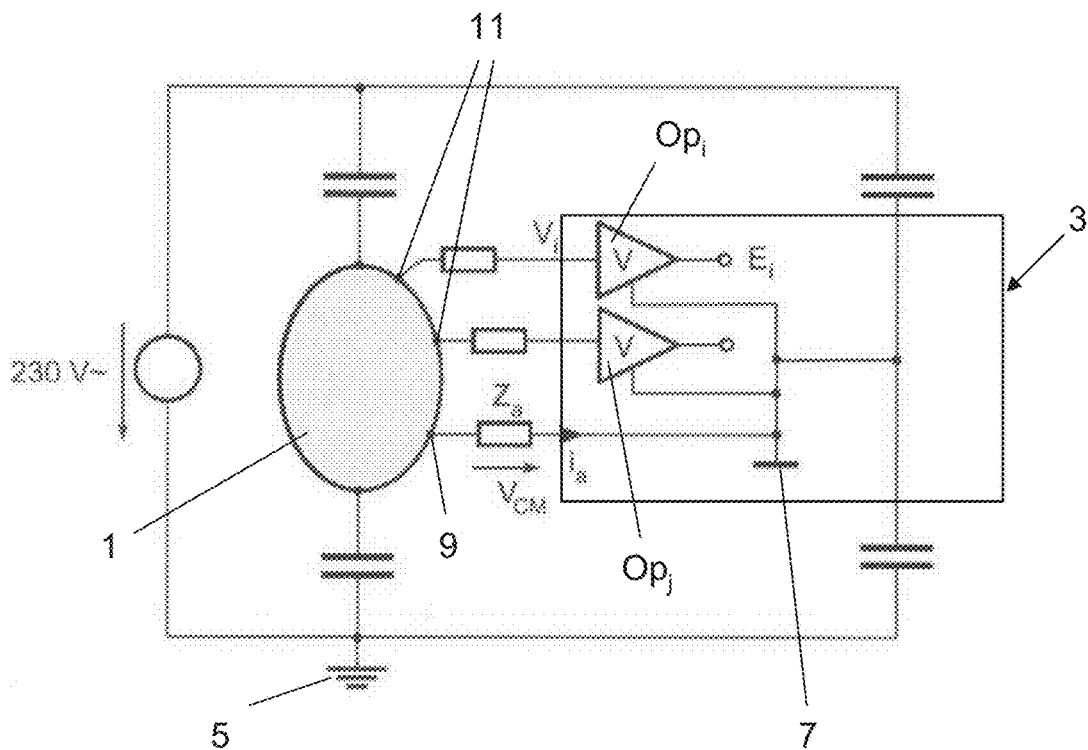
Fig. 1 (State of the ART)
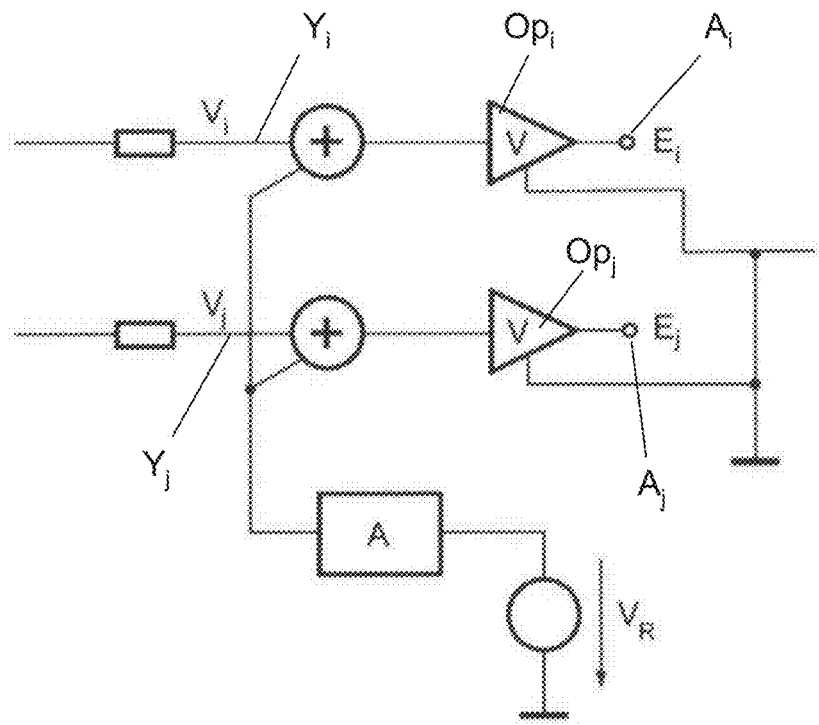
Fig. 2

DEVICE AND METHOD FOR DETECTING ELECTRIC POTENTIALS

CROSS REFERENCE TO RELATED APPLICATIONS

This application is a United States National Phase Application of International Application PCT/EP2015/001340 filed Jul. 2, 2015, and claims the benefit of priority under 35 U.S.C. § 119 of German Patent Application DE 10 2014 009 955.5 filed Jul. 7, 2014, the entire contents of which are incorporated herein by reference.

FIELD OF THE INVENTION

The present invention pertains to a device for detecting electric potentials of the body of a patient having a plurality of inputs for connection with measuring electrodes, which may be placed on the body of a patient, and having a plurality of outputs, whereby each of the inputs is connected with an output via an amplifier, whereby a summing unit is provided, which is connected with the outputs and which is designed to output a mean value of the signals of the outputs of the amplifiers. The present invention also pertains to a method for detecting potentials.

BACKGROUND OF THE INVENTION

When potentials are to be measured, for example, on the skin of a patient and the useful signal contained in these potentials lies in the mV range, as this may be the case in an electrocardiogram (ECG) or an electromyogram (EMG), the following problems arise.

As the body of the patient is surrounded by electric fields, potentials form due to capacitive coupling on the skin of the patient. This effect can generally be described as the body being coupled capacitively, particularly to a 230V/50 Hz-alternating current voltage field, which is caused by power supply sources located in the surrounding area of the patient. For the sake of safety, the patient is not coupled to a uniform surrounding area ground, since this would cause a considerable risk to the patient.

In addition, the problem arises that a measuring device, with which the electrodes on the skin of the patient are connected, has to be galvanically separated from a surrounding area ground. This in turn results in the measuring device, with an internal ground, also being capacitively coupled to the surrounding area. The problem arises that the device ground lies at a potential, that is at a level that is not known and which generally differs from the potential of the patient.

In order to in this case at least achieve that the patient and the ground of the measuring device are at the same potential, or that at least a fixed potential difference is present between both, it is known to connect the device ground and the body of the patient with one another via an additional electrode. This is shown in FIG. 1. Since, however, the device ground and the patient may generally be at a different potential, because of the inhomogeneity of the surrounding fields, which arises from the different capacitive coupling to the surrounding area, a compensating current flows. This leads to a so-called common mode signal because of the impedance of the coupling to the patient via the electrode. This common mode signal is amplified by the amplifiers in the measuring device. When the useful signals actually to be detected with the measurement are very small, the common mode signal leads to the actual useful signal no longer being able to be resolved. In addition, the difficulty arises that the amplifiers have to be high dynamics amplifiers, so that the useful signal and the higher common mode signal overlaying same can be processed. Furthermore, a digital electronic analyzer arranged downstream has to provide a high number of bits per measured value in order to be able to process the large signals.

Furthermore, it is known from the state of the art of DE 29 26 165 A1 to subtract the mean value of the signals that are output by the amplifiers from the input signals of the amplifiers. In this case, however, there is also the problem that the common mode signal is not amplified, but nevertheless is output together with the useful signal at the output of the amplifier. When the useful signal is extremely small, this can lead to the level of the common mode signal and that of the amplified useful signal nevertheless being on the same order of magnitude, so that these cannot be separated from one another easily. Besides, there is the problem that the amplifiers and an electronic analyzer arranged downstream have to be adapted to further process the comparatively large common mode signal as well.

SUMMARY OF THE INVENTION

Based on the above, an object of the present invention is to design a measuring device for the detection of potentials, such that common mode signals are reliably removed from the signal.

According to a first aspect of the present invention, this object is accomplished by a subtracting unit being provided, which is arranged downstream of a summing unit and is configured to subtract the output of the summing unit, amplified by an amplification factor, from at least a portion of an output of the subtracting unit (from the output of the subtracting unit or from an attenuated output of the subtracting unit). The output of the subtracting unit is connected with the inputs of the amplifiers. The amplification factor in the subtracting unit and an amplification of the amplifiers is adapted for the output of the subtracting unit, such that the reciprocal value of the amplification factor corresponds to the amplification.

With such a design of the device, it is achieved that a signal, which no longer contains any common mode signal component, is output at each of the outputs of the amplifiers. This is a result of the fact that a uniform additional reference signal, which is adapted to compensate the common mode signal, is sent to all of the inputs of the amplifiers. This adaptation is carried out on the basis of the following considerations.

The input signals $V_i$ detected at the inputs of the amplifiers are composed of the actual useful signal $V_{si}$ and a common mode signal $V_{cm}$, which is identical at all inputs of the amplifiers. In addition, according to the present invention, an additional reference signal $V_r$ is added to all inputs. Thereby, the input signal $V_i$ in the amplifiers is amplified by an amplification factor $\alpha$ and the reference signal $V_r$ is amplified by an amplification factor $\beta$. For the signals at the outputs of the amplifiers, the result is $$E_i = \alpha \cdot V_i + \beta \cdot V_r = \alpha \cdot V_{si} + \alpha \cdot V_{cm} + \beta \cdot V_r.$$

For the mean value $\overline{E_i}$ over all output signals $E_i$, it is true in a measurement of the potentials on the body of a patient that $\overline{Ei} = \alpha \cdot V_{cm} + \beta \cdot V_r$.

Basically then no common mode signal component is contained in the individual input signals when $\overline{E_i} = 0$. This leads to an optimal value $V_{r,opt}$ for the reference signal being obtained by $$V_{r,opt} = -\frac{\alpha}{\beta} \cdot V_{cm}.$$

However, this assumes that $V_{cm}$ is known. Another possibility arises from the second equation for $\overline{E}_i$, which can be resolved to $V_{cm}$, so that in case of an at first randomly selected $V_r$, the equation $$V_{cm} = \frac{\overline{E}_i}{\alpha} \cdot - \frac{\beta}{\alpha} \cdot V_r$$

arises for $V_{cm}$, with which $V_{cm}$ can be determined. This may now be used by the expression for $V_{cm}$ being inserted into the equation for $V_{r,opt}$, so that $$V_{r,opt} = V_r - \frac{\overline{E}_i}{\beta}$$

is obtained.

This equation permits a recursive determination of $V_{r,opt}$, which is particularly implemented by the device according to the present invention, in which the mean value of the output signals $\overline{E}_i$, which is amplified by an amplification factor $1/\beta$, is subtracted from the reference signal $V_r$, whereby this amplification factor corresponds precisely to the reciprocal value of the amplification for the reference signal. According to the present invention, this requirement is particularly implemented in the subtracting unit.

The result in such a setting of the reference signal is that the mean value $\overline{E}_i$ becomes zero and thus the individual output signals are free from common mode signals. Thus, the problems explained above with regard to the dynamics of the amplifiers and the requirements on the electronic analyzer arranged downstream are eliminated with the device according to the present invention.

In a preferred embodiment of the device according to the present invention, the subtracting unit is configured in such a way that the output of the summing unit, amplified by an amplification factor, is subtracted from an output of the subtracting unit, multiplied by a factor s, which is less than one. When the output of the subtracting unit is recoupled to the input of the subtracting unit in a non-attenuated manner, there is the risk that the entire system does not operate in a stable manner. It is therefore preferred to provide an attenuation at this point—such that the output of the summing unit, amplified by an amplification factor, is subtracted from a portion of an output of the subtracting unit (an attenuated output of the subtracting unit).

In a further preferred manner, the subtracting unit may be designed as an analog amplifier circuit, which has an inverting adder and an inverter arranged downstream of same, whereby the output of the inverter is connected with the input of the inverting adder and with the inputs of the amplifiers, to which the measuring electrodes can be connected. This represents a simple embodiment of the subtracting unit with analog components.

Further, according to another preferred embodiment, an impedance converter, which may especially be formed by an operational amplifier, may be provided between the output and the input of the subtracting unit. The output of the subtracting unit is consequently only minimally burdened.

Further, it is preferred that the inputs of the subtracting unit have a low-pass filter. Consequently, signal components of high frequency, which come either from the output of the subtracting unit or from the summing unit, are filtered out and do not have an effect on the setting of the reference signal.

On the one hand, it is possible to embody the summing unit as an analog amplifier circuit, in which the signals of the amplifiers are fed to the non-inverting input of an operational amplifier. On the other hand, it is, however, possible to form the summing unit by a digital signal processor as well, whereby the outputs of the amplifiers are connected via analog-digital converters with the inputs of the digital signal processor, whereby the subtracting unit is then designed as an analog amplifier circuit and whereby the output of the digital signal processor is connected with the subtracting unit via a digital-analog converter. Such a design of the summing unit may also be accomplished in a simple manner.

Further, in an alternative preferred embodiment, the summing unit and the subtracting unit may be formed by a digital signal processor, whereby the outputs of the amplifiers are connected with the inputs of the digital signal processor via analog-digital converters and the output of the signal processor is connected via a digital-analog converter with the inputs of the amplifiers. In this case, the entire combination of summing unit and subtracting unit is embodied by a single digital signal processor. In this case the output of the subtracting unit is again returned to an input of the subtracting unit by means of software, and the output may be attenuated in the return in order to guarantee stability.

According to another aspect of the present invention, the object mentioned in the introduction is accomplished by a method for detecting electric potentials at a plurality of measuring electrodes, whereby the signals of the measuring electrodes are amplified with amplifiers, whereby a mean value signal of the signals of the outputs of the amplifiers is formed, whereby a reference signal is produced by subtracting the mean value amplified by an amplification factor, from the reference signal, whereby the reference signal is fed to the inputs of the amplifiers, and whereby the amplification factor in the subtraction and the amplification of the amplifiers for the reference signal are adapted, such that the reciprocal value of the amplification factor corresponds to the amplification. The advantages already explained in connection with the device according to the present invention are likewise achieved with this method for detecting electric potentials.

The present invention is explained below on the basis of a drawing, which shows only preferred exemplary embodiments. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

FIG. 1 is a schematic view showing a device according to the state of the art;

FIG. 2 is a schematic circuit diagram showing principles of the present invention;

DESCRIPTION OF THE PREFERRED EMBODIMENTS

Figure 3:
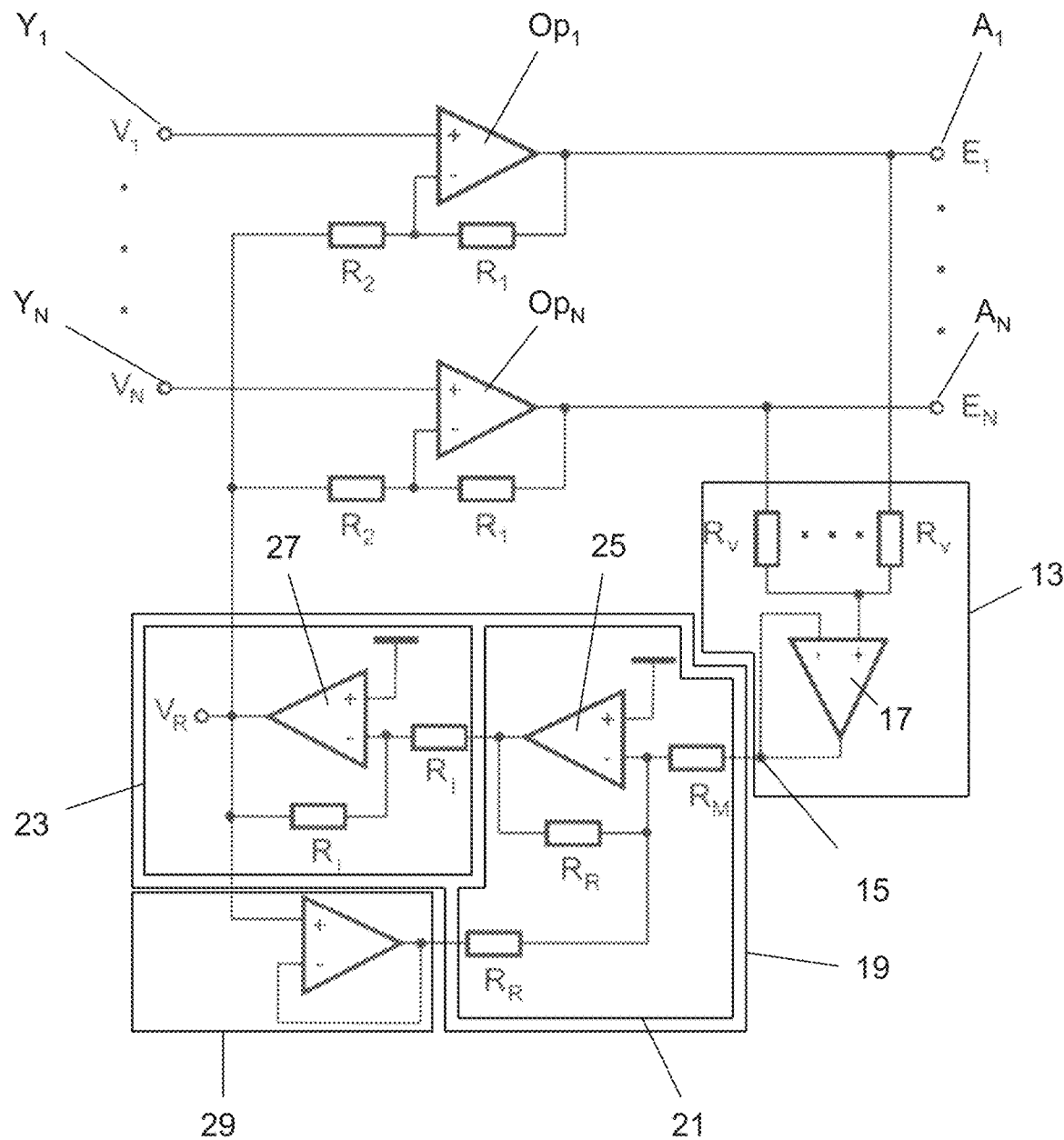
FIG. 3 is a circuit diagram of a first exemplary embodiment of a device according to the present invention.

Referring to the drawings, at first, the basic problem in the detection of small voltage signals, for example, on the body 1 of a patient, shown only schematically here, is disclosed in FIG. 1. It is shown thereby that both the patient 1 and the measuring device 3 are galvanically separated from the surrounding area ground 5, which is also absolutely necessary for the sake of safety. The result of this is that both the body 1 of the patient and the measuring device 3 are capacitively coupled to the surrounding area, so that a potential is formed at both. The ground 7 of the measuring device 3 is connected with the body 1 of the patient via an electrode 9. This leads to a current $i_a$ between the body 1 of the patient and the measuring device 3 because of the impedance $Z_a$ of the electrode 9. This in turn results in a common mode signal $V_{cm}$, which is detected at the actual measuring electrodes 11 and is amplified in the amplifiers $Op_i$ and thus is also contained in the output signals thereof.

By contrast, the present invention adds a reference signal $V_r$ to the signals $V_i$-$V_j$ which are detected at the measuring electrodes 11. The reference signal $V_r$ is adapted such that the reference signal $V_r$ compensates the common mode signal, so that the signals $E_i$-$E_j$ at the outputs $A_i$-$A_j$ of the amplifiers $Op_i$-$Op_j$ no longer contain any common mode signal component. This is first only schematically shown in FIG. 2.

A circuit diagram of the first exemplary embodiment of the device according to the present invention is shown in FIG. 3. A summing unit 13 outputs a mean value, at summing unit output 15, of the output signals $E_1, \ldots, E_n$ of the amplifiers $Op_1, \ldots, Op_n$, is arranged downstream of the amplifiers $Op_1, \ldots, Op_n$. The summing unit 13 is connected to the amplifiers $Op_1, \ldots, Op_n$, which amplify the input signals $V_1, \ldots, V_n$, present at the inputs $Y_1, \ldots, Y_n$. In this case, the summing unit 13 is designed as an analog circuitry device with an operational amplifier 17. The output signals $E_1, \ldots, E_n$ are fed to the non-inverting input of the operational amplifier 17 via suitably selected resistances $R_v$.

The mean value signal generated in the summing unit 13 is fed to a first input of a subtracting unit 19, which is likewise designed as an analog circuitry device in this exemplary embodiment. The subtracting unit 19 comprises an inverting adder 21 as well as an inverter 23, both of which have a correspondingly connected operational amplifier 25, 27.

Besides receiving an input of the mean value signal generated in the summing unit 13, the output signal of the subtracting unit 19 is fed to the input of the subtracting unit 19 via an impedance converter 29, whereby the output signal of the subtracting unit 19 is not amplified or attenuated as a result of the two resistances $R_R$ of the inverting adder 21 being almost identical. However, in a preferred embodiment, these resistances may be selected to be slightly different in order to achieve a slight attenuation of the output signal of the subtracting unit 19, which portion of the output signal of the subtracting unit, or attenuated output signal is again fed to its input, i.e., the output signal is multiplied by a factor s less than one.

The mean value signal generated by the summing unit 13 is amplified in the subtracting unit 19 by an amplification factor up, which is established by the ratio $R_R/R_M$. The signal output by the inverting adder 21 is then still inverted by the inverter 23 arranged downstream, so that the subtracting unit 19 then outputs a reference signal $V_r$ to the subtracting unit output. The reference signal $V_r$ is fed to the inverting inputs of the amplifiers $Op_1, \ldots, Op_n$ at their inverting inputs. This reference signal $V_r$ is then amplified in the amplifiers $Op_1, \ldots, Op_n$ in the known manner by an amplification $\beta'=-R_1/R_2$.

According to the present invention, the resistances $R_1$, $R_2$, $R_R$ and $R_M$ are selected, such that $$R_M = R_R \cdot \frac{R_1}{R_2}$$

applies.

It is consequently fulfilled that the amplification factor $1/\beta$ corresponds to the reciprocal value of the amplification $\beta'$. Thus, the considerations which were already explained above apply, by the reference signal $V_r$ being precisely recursively optimized thereby, by the mean value signal amplified by the amplification factor $1/\beta$ being subtracted from an at first preset reference signal, whereby this amplification factor precisely corresponds to the reciprocal value of the amplification, with which the reference signal is amplified in the amplifiers at the input of the measuring device. Consequently, it is achieved that the output signal $E_1, \ldots, E_n$ output at the outputs $A_1, \ldots, A_n$ is free from common mode components.

Figure 4:
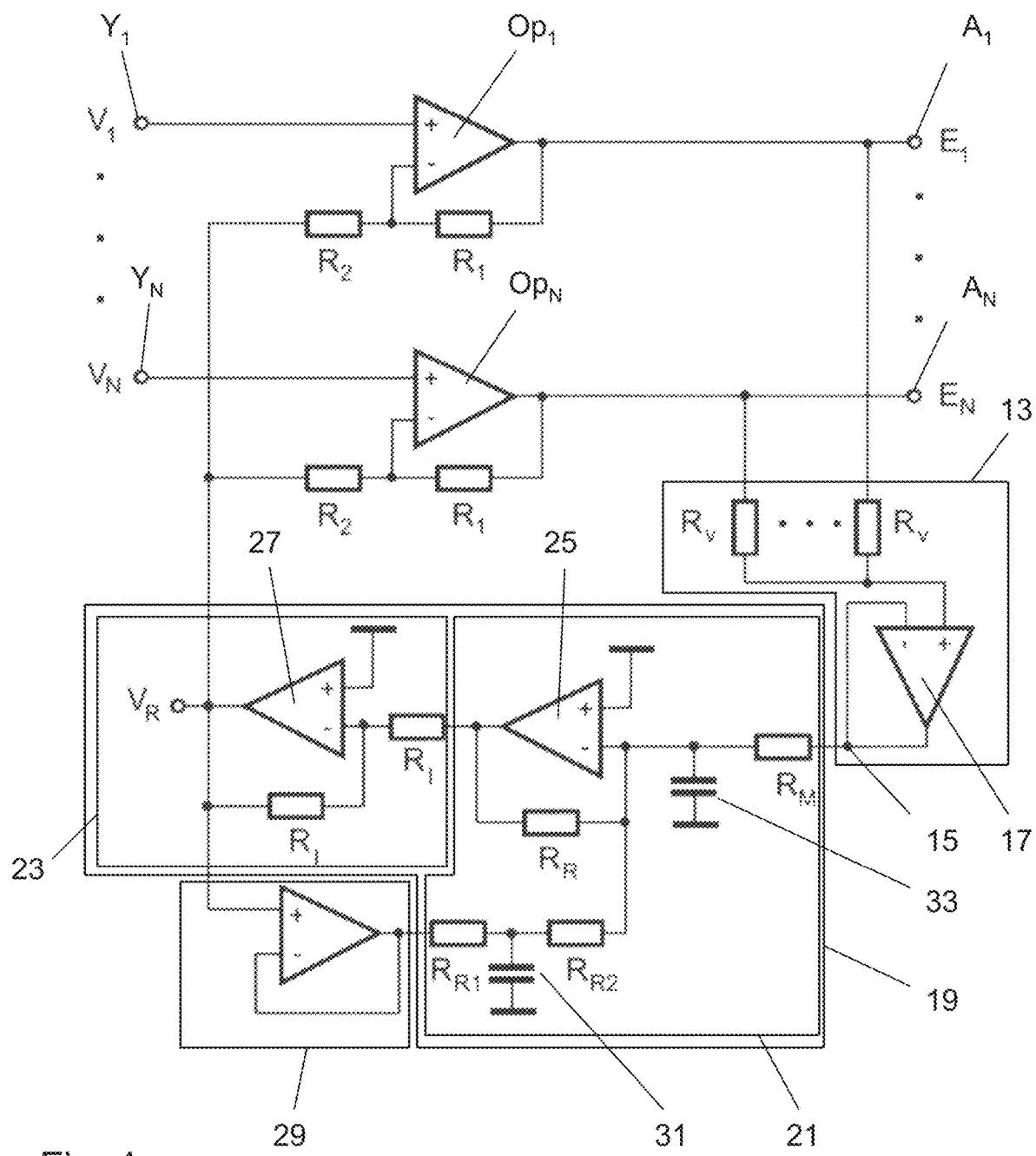
FIG. 4 is a circuit diagram of a second exemplary embodiment of a device according to the present invention.

A circuit diagram of the second exemplary embodiment of a measuring device according to the present invention is shown in FIG. 4. The second exemplary embodiment differs from the first exemplary embodiment only in that the inputs of the subtracting unit 19 and thus in this case the inputs of the inverting adder 21 have low-pass filters 31, 33, so that components of high frequency, which are contained in the mean value signal output by the summing unit 13 as well as that of the output of the subtracting unit 19, are suppressed.

Besides, provisions are made in this second exemplary embodiment for the input of the subtracting unit 19 or of the inverting adder 21, which is connected with the output of the subtracting unit 19, to be formed by two resistances, $R_{R1}$, $R_{R2}$, such that the output signal of the subtracting unit 19 and thus the reference $V_r$ is attenuated, since the resistances $R_{R1}$ and $R_{R2}$ are selected, such that their sum is slightly greater than $R_R$. Thus, an attenuation of the reference signal is achieved in order to ensure that the device operates in an overall stable manner.

Figure 5:
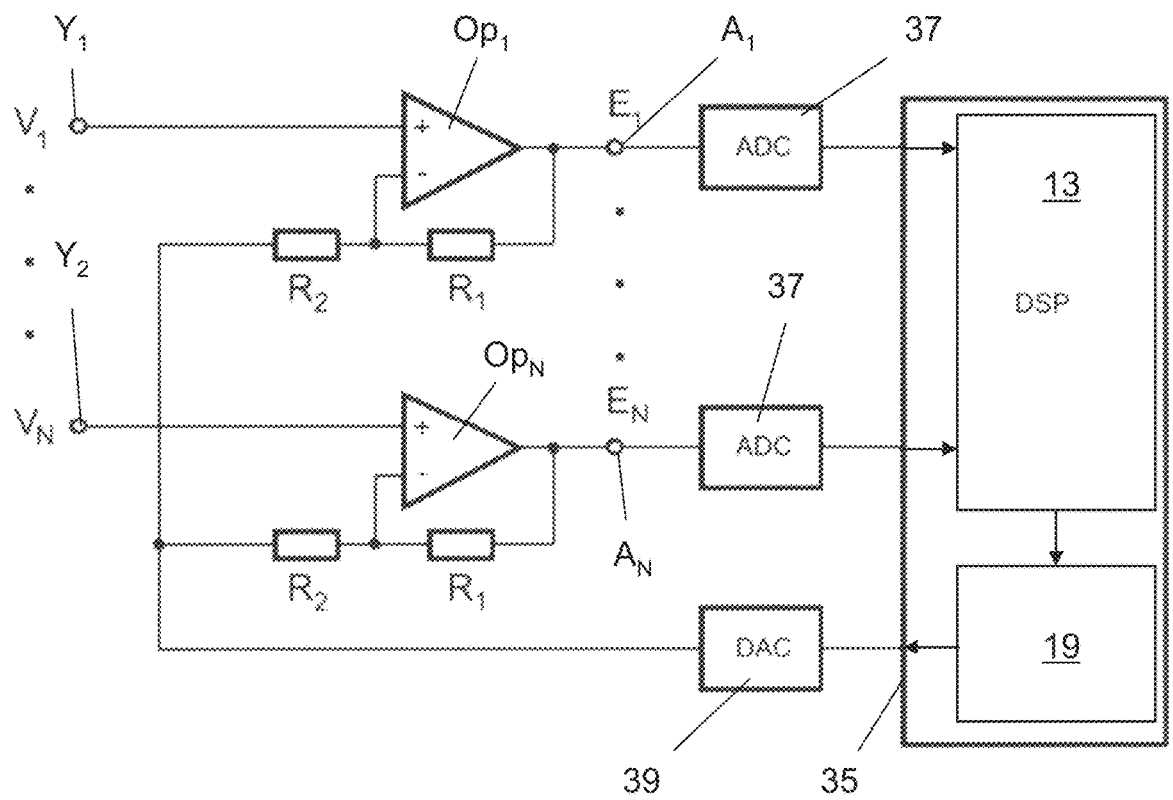
FIG. 5 is a circuit diagram of a third exemplary embodiment of a device according to the present invention.

A circuit diagram of the third exemplary embodiment s shown in FIG. 5. The summing unit 13 and the subtracting unit 19 are formed by a digital signal processor 35, in which the functions of the summing unit 13 and those of the subtracting unit 19 are executed by software. However, in this case, the programming is selected, such that the mean value generated by the summing unit 13 is amplified by the amplification factor $1/\beta$ before it is subtracted from a reference value, whereby this amplification factor likewise corresponds to the reciprocal value of the amplification, with which the reference signal fed to the amplifiers $Op_1, \ldots, Op_n$ is amplified. The outputs $A_1, \ldots, A_n$ are connected with the digital signal processor 35 via analog-digital converters 37 in this third exemplary embodiment. Furthermore, a digital-analog converter 39 is provided, with which the reference signal $V_r$ is converted from a digital signal into an analog signal, in order to subsequently feed this signal to the $Op_1, \ldots, Op_n$.

Figure 6:
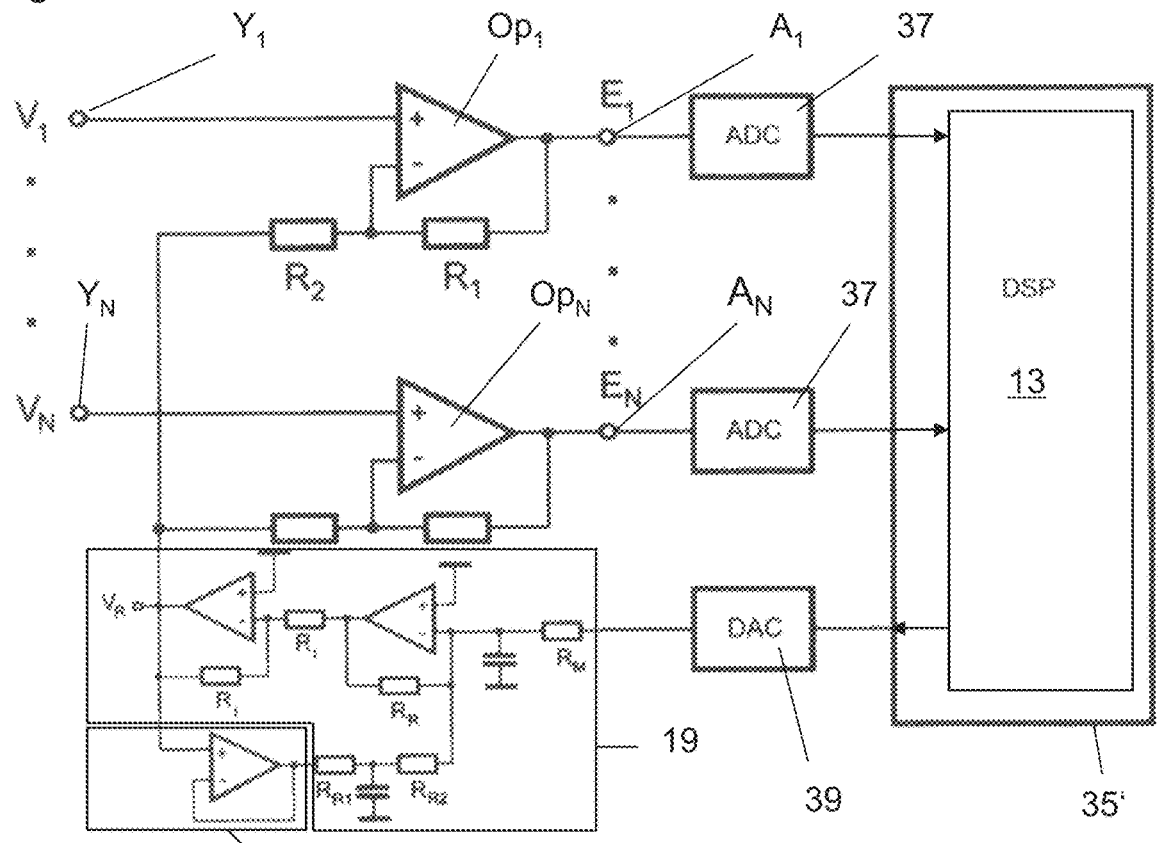
FIG. 6 is a circuit diagram of a fourth exemplary embodiment of a device according to the present invention.

A circuit diagram of the fourth exemplary embodiment is shown in FIG. 6. The summing unit 13 can be embodied alone by a digital signal processor 35', whose inputs are connected with the outputs $A_1, \ldots, A_n$ via an analog-digital converter 37. The mean value signal calculated in the signal processor 35' is again sent to the subtracting unit 19, which is designed as analog circuitry in this case, via a digital-analog converter 39. This subtracting unit 19 is designed corresponding to the second exemplary embodiment (see FIG. 4), which explanation is hereby referenced. In particular, the relationship of the resistances $R_1$, $R_2$, $R_M$ and $R_R$ is selected in such a way as this has already been described in connection with the first exemplary embodiment, so that $$R_M = R_R \cdot \frac{R_1}{R_2}$$

applies.

Thus, all exemplary embodiments have in common that in the detection of electric potentials at the inputs $Y_1, \ldots, Y_2$ of the measuring device, the signals are amplified by amplifiers $Op_1, \ldots, Op_n$, whereby a mean value signal of the outputs $A_1, \ldots, A_n$ of the amplifiers $Op_1, \ldots, Op_n$ is thereby formed. A reference signal $V_r$ is subsequently generated recursively in such a way that the mean value previously generated, amplified by an amplification factor $1/\beta$, is subtracted from at least a portion of the reference signal $V_r$ and this recursively generated reference signal $V_r$ is fed to the inputs of the amplifiers $Op_1, \ldots, Op_n$. In these amplifiers $Op_1, \ldots, Op_n$, the reference signal is amplified by an amplification factor $\beta$ in relation to the outputs $A_1, \ldots, A_n$. In this case, the measuring device is thereby designed, such that the amplification $\beta'$ corresponds to the reciprocal value of the amplification factor $1/\beta$.

The above-described exemplary embodiments of measuring devices are each connected with the advantage that, due to the design of the device, a reference signal $V_r$ is generated, which leads to a signal being generated at the outputs $A_1, \ldots, A_n$, which is free from common mode components.

While specific embodiments of the invention have been shown and described in detail to illustrate the application of the principles of the invention, it will be understood that the invention may be embodied otherwise without departing from such principles.

The invention claimed is:

1. A device for detecting the electric potentials of the body of a patient, the device comprising:
   a plurality of device inputs for connection with measuring electrodes, which measuring electrodes may be placed on the body of a patient;
   a plurality of amplifiers;
   a plurality of device outputs, each of the device inputs being connected with one of the device outputs via one of the amplifiers;
   a summing unit having a summing unit input connected with each of the outputs, the summing unit providing a summing unit output that is a mean value of the signals by the amplifiers; and
   a subtracting unit connected to the summing unit, the subtracting unit subtracting an output of the summing unit, amplified by an amplification factor, from at least a portion of an output of the subtracting unit, wherein:
   the output of the subtracting unit is connected with inputs of the amplifiers having an amplifier amplification; and
   the amplification factor is a reciprocal value of the amplifier amplification.

2. A device in accordance with claim 1, wherein the subtracting unit is configured, such that the output of the summing unit, amplified by an amplification factor, is subtracted from the output of the subtracting unit multiplied by an attenuation factor, which attenuation factor is less than one.

3. A device in accordance with claim 1, wherein:
   the subtracting unit is comprised of an analog amplifier circuit comprised of an inverting adder and an inverter; and
   an output of the inverter is connected with the input of the inverting adder and connected with the inputs of the amplifiers.

4. A device in accordance with claim 1, further comprising an impedance converter connected between the output of the subtracting unit and an input of the subtracting unit.

5. A device in accordance with claim 1, wherein the subtracting unit further comprises a low-pass filter at a subtracting unit input, connected to the summing unit, and a low pass filter at a subtracting unit input, connected to the output of the subtracting unit.

6. A device in accordance with claim 1, further comprising:
   an analog-digital converter; and
   digital-analog converters, wherein:
   the summing unit is formed by a digital signal processor;
   outputs of the amplifiers are connected with inputs of the digital signal processor via the analog-digital converters;
   the subtracting unit is configured as an analog amplifier circuit; and
   an output of the digital signal processor is connected with the subtracting unit via the digital-analog converter.

7. A device in accordance with claim 1, further comprising:
   analog-digital converters; and
   a digital-analog converter, wherein:
   the summing unit and the subtracting unit are formed by a digital signal processor;
   outputs of the amplifiers are connected with inputs of the digital signal processor via the analog-digital converters; and
   an output of the digital signal processor is connected with the inputs of the amplifiers via the digital-analog converter.

8. A method for detecting electric potentials from signals of a plurality of measuring electrodes, the method comprising:
   amplifying the signals of the measuring electrodes with amplifiers;
   forming a mean value signal of signals of outputs of the amplifiers;
   producing a reference signal by subtracting the mean value signal, amplified by an amplification factor, from at least a portion of the reference signal;
   feeding the reference signal to inputs of the amplifiers, wherein:
   the reference signal is amplified by an amplification by the amplifiers; and
   the amplification of the amplifiers for the reference signal is the reciprocal value of the amplification factor.

9. A method in accordance with claim 8, wherein the reference signal is attenuated before the subtraction by a factor, wherein the factor is less than one.

10. A method in accordance with claim 8, wherein the reference signal and the mean value signal are filtered by a low-pass filter before the subtraction.

11. A device for detecting electric potentials of a body of a patient, the device comprising:
 a plurality of electrode inputs configured to connect with measuring electrodes;
 a plurality of amplifiers, each of said plurality of amplifiers being configured to receive a separate electric potential from the body of the patient, said each amplifier also being configured to receive a reference voltage, said each amplifier also being configured to amplify the reference voltage by an amplification factor, said each amplifier also having an amplifier output forming a respective device output;
 a summing unit connected with each of said amplifier outputs, said summing unit generating a mean value of signals generated by said plurality of amplifiers;
 a subtracting unit generating the reference voltage and transmitting the reference voltage to said each amplifier, said subtracting unit receiving the mean value from the summing unit, said subtracting unit amplifying the mean value by a reciprocal of the amplification factor to create a correction factor, said subtracting unit subtracting the correction factor from a previous reference voltage to generate a new reference voltage, said subtracting unit transmitting the new reference voltage to said each amplifier to replace the previous reference voltage, said subtracting unit recursively operating to replace the new reference voltage with the previous reference voltage.

12. A device in accordance with claim 11, wherein:
 the subtracting unit is comprised of an analog amplifier circuit comprised of an inverting adder and an inverter; and
 an output of the inverter is connected with the input of the inverting adder and connected with the inputs of the amplifiers.

13. A device in accordance with claim 11, further comprising an impedance converter connected between an output and an input of the subtracting unit.

14. A device in accordance with claim 11, wherein the subtracting unit further comprises a low-pass filter connected to an output of the summing unit, and a low pass filter connected to a reference signal input of the subtracting unit.

15. A device in accordance with claim 11, further comprising:
 an analog-digital converter; and
 a digital-analog converters, wherein:
 the summing unit is formed by a digital signal processor;
 outputs of the amplifiers are connected with inputs of the digital signal processor via the analog-digital converters;
 the subtracting unit is configured as an analog amplifier circuit; and
 an output of the digital signal processor is connected with the subtracting unit via the digital-analog converter.

16. A device in accordance with claim 11, further comprising:
 analog-digital converters; and
 a digital-analog converter, wherein:
 the summing unit and the subtracting unit are formed by a digital signal processor;
 outputs of the amplifiers are connected with inputs of the digital signal processor via the analog-digital converters; and
 an output of the digital signal processor is connected with the inputs of the amplifiers via the digital-analog converter.

17. A device in accordance with claim 11, wherein;
 said subtracting unit is configured to amplify the previous reference voltage by an attenuation factor being less than one.

18. A device in accordance with claim 11, wherein;
 each said respective device output providing a signal from a respective one of the measuring electrodes without common mode components.

* * * * *